United States Patent

Guise

[11] 4,144,268
[45] Mar. 13, 1979

[54] PREPARATION OF BISULPHITE ADDUCTS OF BIRUET-POLYISOCYANATES

[75] Inventor: Geoffrey B. Guise, Highton, Australia

[73] Assignee: Commonwealth Scientific and Industrial Research Organization, Campbell, Australia

[21] Appl. No.: 766,537

[22] Filed: Feb. 7, 1977

[30] Foreign Application Priority Data

Feb. 11, 1976 [AU] Australia .............................. PC4815

[51] Int. Cl.$^2$ .......................................... C07C 143/02
[52] U.S. Cl. ................................ 260/513 N; 8/128 A; 260/453 AB; 528/46
[58] Field of Search ................. 260/453 AB, 77.5 TB, 260/508, 513 N

[56] References Cited

U.S. PATENT DOCUMENTS

| | | | |
|---|---|---|---|
| 2,710,816 | 6/1955 | Evans et al. | 260/775 TB |
| 2,746,988 | 5/1956 | Doser et al. | 260/513 |
| 3,898,197 | 8/1975 | Guise et al. | 260/77.5 TB |
| 3,984,365 | 10/1976 | Lienert et al. | 260/77.5TB |

Primary Examiner—Dolph H. Torrence
Attorney, Agent, or Firm—Dennis P. Clarke

[57] ABSTRACT

Bisulphite adducts of biuret-polyisocyanates are prepared by reacting an aqueous solution containing more than 200 gm/l. of sodium bisulphite with a selected alcohol and a biuret-polyisocyanate having one of the following structures:

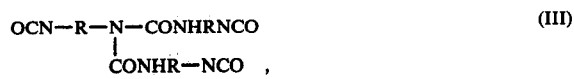

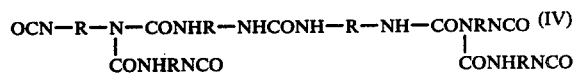

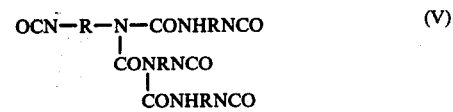

wherein R in each occurrence is the same or different divalent alkyl, cycloalkyl, aryl or aralkyl radical. A preferred adduct is the adduct of N,N',N"-tris(6-isocyanatohexyl) biuret. The adducts are useful for the treatment of fibrous materials, particularly as shrink-resisting agents, for surface coatings and for forming elastomers.

12 Claims, No Drawings

PREPARATION OF BISULPHITE ADDUCTS OF BIURET-POLYISOCYANATES

This invention describes methods to prepare polycarbamoyl sulphonates from polyisocyanates containing biuret groups of structure I where R is a divalent organic radical and the X groups may be either hydrogens or —CONXR—NCO groups. The formation of a carbamoyl sulphonate or bisulphite adduct from an isocyanate is shown schematically in equation (i).

$$\text{OCN-R-NCO-NX-R-NCO} \atop \text{CONX-R-NCO} \qquad \text{I}$$

$$\text{OCN-(CH}_2)_6\text{-NCO-NH(CH}_2)_6\text{NCO} \atop \text{CONH(CH}_2)_6\text{NCO} \qquad \text{II}$$

$$\text{R'NCO} + \text{NaHSO}_3 \longrightarrow \text{R'NHCOSO}_3^- \text{Na}^+ \qquad (i)$$

In German Pat. No. 1,101,394 the formation of biuret-polyisocyanates of structure I from diisocyanates of the type R(NCO)$_2$ and water was described. Improved methods to prepare I by heating diisocyanates and tertiary alcohols were described in German Pat. Nos. 1,543,178, 1,931,055 and 2,308,015 (= Australian Pat. No. 65504/74). The biuret-polyisocyanate of structure II (i.e., N,N',N''-tris(6-isocyanatohexyl)biuret) derived from hexamethylene diisocyanate is used extensively in polyurethane surface coatings and elastomers.

Reaction (i) has been long known for simple isocyanates (S. Petersen, Liebigs Annalen, 562, 1949 p.205 et seq.), but I, when reacted with aqueos bisulphite, hydrolyses instead of forming carbamoyl sulphonates. In our Australian Pat. No. 460,168, methods and described to prepare the bisulphite adducts of polyisocyanate prepolymers containing on average at least two isocyanate groups, these prepolymers being prepared from the reaction of a polyisocyanate and a polyhydroxy compound. When the methods of Austrailian Pat. No. 460,168 are used to convert I into polycarbamoyl sulphonates there is either extensive side reactions of the isocyanates to form products other than carbamoyl sulphonates, or the methods yield dilute solutions (10% solids content or less) of the polycarbamoyl sulphonates, and it is necessary to concentrate these solutions in a subsequent separate step in order to obtain a product suitable for use. Such concentration operations may lead to the decomposition of some of the carbamoyl sulphonate groups.

We have now found improved methods to prepare certain bisulphite adducts of I which are characterised by high conversions of the isocyanate groups into bisulphite adducts and the formation directly of concentrated solutions of these bisulphite adducts. Accordingly the present invention provides methods in which components A, B and C as described below are mixed and allowed to react.

Component A is one or more biuret-polyisocyanates of structure III, IV or V (see below) where the R groups are the same or different divalent alkyl, cycloalkyl, aryl or aralkyl radical or radicals. The preferred components A are biuret-triisocyanates of structure III, in particular N, N',N''-tris(6-isocyanatohexyl)biuret. The most preferred components A are mixtures containing at least 80% by weight of III. The most preferred R groups are the isomeric tolylenes, —(CH$_2$)$_n$— where n is from 4 to 12 inclusive or the divalent radicals VI or VII.

$$\text{OCN-R-N-CONHRNCO} \atop \text{CONHR-NCO} \qquad \text{III}$$

$$\text{OCN-R-N-CONHR-NHCONH-R-NH-CONRNCO} \atop \text{CONHRNCO} \qquad \text{CONHRNCO} \qquad \text{IV}$$

$$\text{OCN-R-N-CONHRNCO} \atop \text{CONRNCO} \atop \text{CONHRNCO} \qquad \text{V}$$

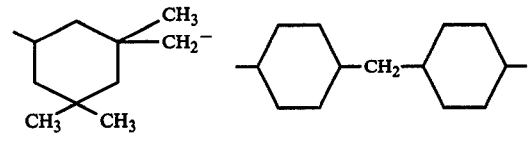

VI                                           VII

Component B is one of the following alcohols, or a mixture of two or more of these alcohols.
(i) ethanol
(ii) isopropanol
(iii) ethylene glycol monomethyl ether
(iv) ethylene glycol monoethyl ether
(v) diethylene glycol monoethyl ether
(vi) tetrahydrofurfuryl alcohol.
The preferred component B is (iv), (v) or (vi).

Component C is an aqueous solution containing more than 200 grams per litre at 20° C. of sodium bisulphite, and most preferably more than 350 g/l.

The proportions of components A, B and C are such that the mixture so formed contains more than 20% by weight of non-volatile substances. Immediately before mixing each component is at a temperature in the range −20° to +30° C., preferably each are at ambient temperature. It is also preferable that the mixing of the components is by mechanical means and that such mixing is continued until the reaction is complete.

The preferred biuret-polyisocyanates for component A are prepared by the methods of the German patents listed above from one or more of the following isocyanates — 2,4-tolylene diioscyanate, 2,6-tolylene diisocyanate, or mixtures of these isomers, hexamethylene diisocyanate, isophorone diisocyanate, (1-isocyanato-3-isocyanatomethyl-3,5,5-trimethylcyclohexane), 2-carboxymethylpentamethylene diisocyanate, or one of the isomers of the following diisocyanates, xylylene diisocyanate, phenylene diisocyanate, trimethylhexamethylene diisocyanate, diphenylmethane diisocyanate, cyclohexylene diisocyanates, bis(isocyanatomethyl)-cyclohexanes and methylene-bis-isocyanatocyclohexanes (for example, the commercial product Hylene W (du Pont) which is mainly the 4,4'-isomer).

The most preferred diisocyanate for the preparation of III is hexamethylene diisocyanate, which yields II as well as higher molecular weight products. The commercial product Desmodur N (Bayer A.G., Germany) consists mainly of compound II.

It is to be appreciated that biuret-polyisocyanates III, IV and V so prepared from diisocyanates, may contain a mixture of substances of these structures and in addition, other materials may be present, for example ureas of structure OCN—R—NCHONH—R—NCO and also traces of unreacted diisocyanate.

In addition to the compounds A, B and C the reaction mixture may contain up to 20% by weight of one or more of the following water insoluble solvents, benzene, toluene, xylene, chlorobenzene, chloroform, perchloroethylene, ethyl acetate, ethylene glycol monoethyl ether acetate, ethylene glycol monomethyl ether acetate, and diethylene glycol monoethyl ether acetate.

The components A, B and C, immediately after mixing may not form a homogeneous solution, in contrast to the preferred methods of Australian Pat. No. 460,168 in which the preferred methods involve homogeneous reaction mixtures. Two liquid phases may be present in the reaction mixture or solids such as sodium bisulphite or metabisulphite may separate however, as the reaction proceeds the reaction mixture becomes homogeneous, although in some cases on further standing the polycarbamoyl sulphonate may separate as a separate layer. Such separation enables very concentrated solutions of the polycarbamoyl sulphonates to be obtained.

The bisulphite adducts of biuret-polyisocyanates prepared by the methods of the present invention may be used alone or mixed with other polymers for the treatment of fibrous materials, for surface coatings or to form elastomers. A particularly advantageous application is when mixed with poly(acrylic acid ester) latices for shrink-resisting wool fabrics using the methods of Australian patent application No. 67787/74.

EXAMPLES

Percentages are by weight. The sodium methabisulphite used in the following examples was found iodometrically to be about 95% pure, and the x% sodium metabisulphite solutions used below were prepared by dissolving x grams of this sodium metabisulphite in water and making up to a volume of 100 ml at 20° C.

Biuret-polyisocyanate VIII was prepared from hexamethylene diisocyanate and was used as a 75% solution in a 1:1 mixture of ethylene glycol, monoethyl ether acetate and xylene. This had an isocyanate content of 16.4%. The non-volatile component of VIII contained more than 80% of structure II.

Biuret polyisocyanate IX was prepared from hexamethylene dissocyanate and contained more than 80% of structure II. III contained 100% non-volatile material and had an isocyanate content of 21.4%.

The carbamoyl sulphonate group content of preparations was determined by decomposing a sample with alkali and estimating the sulphite released iodometrically. A 2g sample of the preparation was dissolved in a mixture of water (70 ml) and isopropanol (100 ml). This solution was then titrated against a 0.05M iodine solution containing potassium iodide to the iodine-colour end point. This titre gives the content of free bisulphite. To the solution from the previous titration, 30% sodium hydroxide (10 ml) was then added. After 2 minutes this was acidified with 25% sulphuric acid (25 ml) and immediately titrated again against 0.05M iodine. The second titre gives the carbamoyl sulphonate content.

EXAMPLE I

This example demonstrates the critical nature of the reaction conditions to obtain high conversions of the isocyanate groups of VIII into carbamoyl sulphonates.

VIII (10g) was dissolved in ethylene glycol monoethyl ether (20 ml) with stirring at room temperature and without delay an aqueous solution containing a 10% excess of sodium metabisulphite was added. Stirring was continued and after an hour a sample was removed and carbamoyl sulphonate group content estimated to give the following results.

| Metabisulphite Concentration g/100 ml | % Conversion of Isocyanate groups into Carbamoyl Sulphonates |
|---|---|
| 10 | 25 |
| 20 | 65 |
| 25 | 70 |
| 30 | 72 |
| 35 | 94 |
| 40 | 95 |
| 50 | 98 |
| 55 | 95 |
| 57 (saturated) | 95 |

It is therefore preferable to use 35% or more concentrated sodium metabisulphite solution.

EXAMPLE II

This example demonstrates the critical nature of solvent in the reaction of VIII with sodium bisulphite.

VIII (10g) was dissolved in the solvent (20 ml) with stirring at room temperature and without delay 40% sodium methabisulphite solution (11 ml) was slowly added. Stirring was continued for an hour, and then a sample was removed and the carbamoyl sulphonate group content estimated with the following results.

| Solvent | % Conversion of Isocyanate Groups into Carbamoyl Sulphonates |
|---|---|
| methanol | 36 |
| ethanol | 89 |
| isopropanol | 56 |
| ethylene glycol monomethyl ether | 67 |
| ethylene glycol monoethyl ether | 95 |
| diethylene glycol monomethyl ether | 62 |
| diethylene glycol monoethyl ether | 97 |
| tetrahydrofurfuryl alcohol | 96 |

In other experiments less than 10% conversion of isocyanate groups into carbamoyl sulphonates was obtained with the following solvents, n-propanol, n-butanol, sec-butanol, t-butanol, benzyl alcohol, acetone, ethylene glycol, dioxan, ethylene glycol dimethyl ether, dimethyl formamide and dimethyl sulphoxide.

Examples III–VII demonstrate the preparation directly of concentrated solutions of the carbamoyl sulphonates from biuret polyisocyanates of structure I.

EXAMPLE III

Polyisocyanate VIII (100g) was dissolved with stirring at room temperature in ethylene glycol monoethyl ether (200 ml) and 40% sodium metabisulphite (110 ml) was added. The reaction mixture was cloudy initially but evolved heat and became homogeneous after 5 minutes.

After 15 minutes the reaction mixture was diluted with water to 25% solids, forming a perfectly clear solution which was stable to prolonged storage at room temperature. Analyses indicated that at least 95% of the isocyanate groups had been converted into carbamoyl sulphonates.

This product on further dilution with water gives a faintly milky solution due to the presence of water insoluble solvents. These can be removed by the following methods.

The 25% solids product is diluted with water to 15–20% solids. On standing the water insoluble solvent separates out as an upper layer which can be separated. Alternatively, to the reaction mixture after about 15 minutes from the commencement of the reaction, isopropanol (500 ml) is added. On standing overnight the carbamoyl sulphonate separates out as a viscous semi-solid lower layer. The upper solvent layer is decanted off and the lower layer is dissolved in a little water to give a 30% solids solution.

Similarly, results are obtained if ethylene glycol monoethyl ether used in this preparation was replaced by tetrahydrofurfuryl alcohol.

EXAMPLE IV

Polyisocyanate VIII (10g) was reacted with 55% sodium metabisulphite (8 ml) in ethylene glycol monoethyl ether (10 ml) as before. Analysis indicated approximately 91% of the isocyanate groups had been converted into carbamoyl sulphonates. This product partly solidified on standing, however, if diluted with water to 30% solids content, a clear solution was obtained.

EXAMPLE V

Polyisocyanate IX (50g) was dissolved in ethylene glycol monoethyl ether (100 ml) and 55% sodium metabisulphite solution (53 ml) was added. The reaction mixture evolved some heat and became homogeneous after 10 minutes. After 80 minutes water (50 ml) was added. This gave a product containing 30% solids. Analysis indicated that 96% of the isocyanate groups were converted into carbamoyl sulphonates.

EXAMPLE VI

Desmodur N (Bayer A.G., Germany) (10g of a 75% solution in a 1:1 ethylene glycol monoethyl ether acetate and xylene) in ethylene glycol monoethyl ether (20 ml) was reacted with 40% sodium metabisulphite solution (11 ml). Approximately 95% of the isocyanate groups were converted into carbamoyl sulphonates. The water insoluble solvents could be removed by the methods in Example III.

EXAMPLE VII

Desmodur N (Bayer A.G., Germany) (7.5g of 100% material) was reacted with 55% sodium metabisulphite solution (8 ml) in ethylene glycol monoethyl ether (15 ml) as before. Analysis indicated that at least 95% of the isocyanates had been converted into carbamoyl sulphonates.

EXAMPLE VIII

The following example demonstrates the use of the bisulphite adducts prepared in the previous experiments to shrink-resist wool by the method of Australian patent application No. 67787/74.

Solutions were prepared containing 3% Primal K3 (Rohm and Haas, a polyacrylic ester latex), 0.5% sodium bicarbonate and the amounts listed below of the polycarbamoyl sulphonates prepared above. These solutions were padded onto samples of plain weave worsted wool fabric (150 g/m$^2$) with a laboratory mangle set to give 100% pick-up. The samples were dried for 5 minutes at 105° and then steam for 1 minute. The samples were then washed for 3 hours in a 50 liter Cubex International machine with 12.5 liter, pH 7.5 wash liquor at 40°. The following area shrinkages were obtained.

| % Polycarbamoyl Sulphonate Solids Added | Area Shrinkage |
| --- | --- |
| None | 70 |
| 0.5% Example I | 0 |
| 1.0% Example I | 1 |
| 0.5% Example II | 1 |
| 0.5% Example III | 1 |
| 0.5% Example IV | 0 |
| 0.5% Example VI | 0 |
| 0.5% Example VII | 1 |
| 0.5% Example VIII | 1 |

Those skilled in the art will appreciate that the invention described herein is susceptible to variations and modifications other than those specifically described. It is to be understood that the invention includes all such variations and modifications which fall within its spirit and scope.

We claim

1. A method for preparing a bisulphite adduct of a biuret-polyisocyanate, said biuret-polyisocyanate being selected from the group consisting of the following members (III), (IV) and (V):

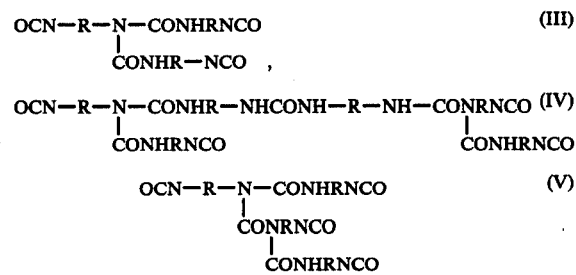

wherein R in each occurrence is the same or different divalent alkyl, cycloalkyl, aryl or aralkyl radical; which method comprises mixing, within the temperature range of −20° to +30° C., and allowing to react:

(A) one or more biuret-polyisocyanates (III), (IV) and (V) as defined above;
(B) one or more alcohols selected from ethanol, isopropanol, ethylene glycol monomethyl ether, ethylene glycol monoethyl ether, diethylene glycol monoethyl ether and tetrahydrofurfuryl alcohol; and
(C) an aqueous solution containing more than 200 grams per liter at 20° C. of sodium bisulphite;

the proportions of components (A), (B) and (C) being such that the mixture so formed contains more than 20% by weight of non-volatile substances.

2. A method as claimed in claim 1 wherein the reaction mixture in addition contains up to 20% by weight of one or more of the following water insoluble solvents: benzene, toluene, xylene, chlorobenzene, chloroform, perchloroethylene, ethyl acetate, ethylene glycol monoethyl ether acetate, ethylene glycol monomethyl ether acetate and diethylene glycol monoethyl ether acetate.

3. A method as claimed in claim 1 wherein R is an isomeric tolylene, —(CH$_2$)$_n$— where n is 4–12, or one of the divalent radicals:

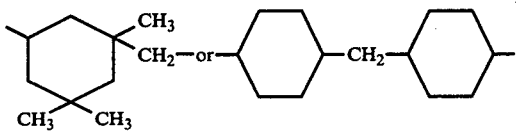

4. A method as claimed in claim 1 wherein component (B) is ethylene glycol monoethyl ether, diethylene glycol monoethyl ether or tetrahydrofurfuryl alcohol.

5. A method as claimed in claim 1 wherein component (C) contains more than 350 grams per liter at 20° C. of sodium bisulphite.

6. A bisulphite adduct of a biuret-polyisocyanate when prepared by the method claimed in claim 1.

7. A method for preparing a bisulphite adduct of N,N',N''-tris(6-isocyanatohexyl)biuret which comprises mixing, within the temperature range of −20° to +30° C., and allowing to react:
 (a) N,N',N''-tris(6-isocyanatohexyl)biuret;
 (b) one or more alchols selected from ethanol, isopropanol, ethylene glycol monomethyl ether, ethylene glycol monoethyl ether, diethylene monoethyl ether and tetrahydrofurfuryl alcohol; and
 (c) an aqueous solution containing more than 200 grams per liter at 20° C. of sodium bisulphite;
the proportions of components (a), (b) and (c) being such that the mixture so formed contains more than 20% by weight of non-volatile substances.

8. A method as claimed in claim 7 wherein the reaction mixture in addition contains up to 20% by weight of a water insoluble solvent selected from the group consisting of benzene, toluene, xylene, chlorobenzene, chloroform, perchloroethylene, ethyl acetate, ethylene glycol monoethyl ether acetate, ethylene glycol monomethyl ether acetate, diethylene glycol monoethyl ether acetate, and mixtures thereof.

9. A method as claimed in claim 7 wherein the mixture contains at least 80% by weight of N,N',N''-tris(6-isocyanatohexyl)biuret.

10. A method as claimed in claim 7 wherein component (b) is ethylene glycol monoethyl ether, diethylene glycol monoethyl ether or tetrahydrofurfuryl alcohol.

11. A method as claimed in claim 7 wherein component (c) contains more than 350 grams per liter at 20° C. of sodium bisulphite.

12. A bisulphite adduct of N,N',N''-tris(6-isocyanatohexyl)biuret whenever prepared by the method claimed in claim 7.

* * * * *